United States Patent
Noguchi et al.

(10) Patent No.: US 11,657,909 B2
(45) Date of Patent: May 23, 2023

(54) MEDICAL IMAGE PROCESSING APPARATUS AND MEDICAL IMAGE PROCESSING METHOD

(71) Applicant: Hitachi, Ltd., Tokyo (JP)

(72) Inventors: Yoshimi Noguchi, Tokyo (JP); Tomofumi Nishiura, Tokyo (JP)

(73) Assignee: FUJIFILM HEALTHCARE CORPORATION, Chiba (JP)

(*) Notice: Subject to any disclaimer, the term of this patent is extended or adjusted under 35 U.S.C. 154(b) by 299 days.

(21) Appl. No.: 17/090,975

(22) Filed: Nov. 6, 2020

(65) Prior Publication Data

US 2021/0241886 A1 Aug. 5, 2021

(30) Foreign Application Priority Data

Jan. 30, 2020 (JP) .............................. JP2020-013424

(51) Int. Cl.
*G16H 30/40* (2018.01)
*G06T 7/00* (2017.01)

(52) U.S. Cl.
CPC .......... *G16H 30/40* (2018.01); *G06T 7/0012* (2013.01); *G06T 2207/30096* (2013.01)

(58) Field of Classification Search
CPC ................. G16H 30/40; G06T 7/0012; G06T 2207/30096
See application file for complete search history.

(56) References Cited

U.S. PATENT DOCUMENTS

| 6,058,322 | A | * | 5/2000 | Nishikawa | ............ | G06T 7/0012 |
| | | | | | | 382/128 |
| 7,146,031 | B1 | * | 12/2006 | Hartman | ................... | G06T 7/73 |
| | | | | | | 378/20 |
| 2014/0142413 | A1 | * | 5/2014 | Chang | .................... | G16H 50/50 |
| | | | | | | 600/407 |
| 2015/0230773 | A1 | * | 8/2015 | Cho | ...................... | G06T 7/0012 |
| | | | | | | 382/128 |
| 2017/0039737 | A1 | * | 2/2017 | Madabhushi | .......... | G06V 10/44 |
| 2021/0350908 | A1 | * | 11/2021 | Kobayashi | ........... | A61B 5/7267 |

FOREIGN PATENT DOCUMENTS

JP 2015-154918 A 8/2015

* cited by examiner

*Primary Examiner* — Vu Le
*Assistant Examiner* — Julius Chai
(74) *Attorney, Agent, or Firm* — Mattingly & Malur, PC

(57) ABSTRACT

To provide a medical image processing apparatus and a medical image processing method enabling a reduction in burden of re-imaging and re-interpretation of a medical image. The medical image processing apparatus for processing a medical image includes: a detection section that detects, from the medical image, a candidate region which is a region including a lesion candidate or target tissue, and that calculates an identification score for the candidate region; a designated region acquisition section that acquires a designated region which is a region designated by an operator; and a redetection section that calculates an identification score for the designated region based on the designated region and multiple predefined regions which are regions used in a process of detecting the candidate region.

6 Claims, 11 Drawing Sheets

|  | PREDEFINED REGION | | | | |
|---|---|---|---|---|---|
|  | FIRST REGION | SECOND REGION | THIRD REGION | ... | nTH REGION |
| TRANSLATION (HORIZON) | 0.2 | 0.5 | 0.1 | ... | 0.1 |
| TRANSLATION (VERTICAL) | 0.4 | 0.5 | 0.2 | ... | 0.2 |
| WIDTH (RATIO) | 1.2 | 0.7 | 1.0 | ... | 1.0 |
| HEIGHT (RATIO) | 0.8 | 1.3 | 1.0 | ... | 1.0 |
| IDENTIFICATION SCORE | 0.8 | 0.9 | 0.1 | ... | 0.1 |

| | PREDEFINED REGION | | | | |
|---|---|---|---|---|---|
| | xTH REGION | yTH REGION | zTH REGION | ... | nTH REGION |
| TRANSLATION (HORIZON) | 0.1 | 0.3 | 0.1 | ... | 0.1 |
| TRANSLATION (VERTICAL) | 0.3 | 0.2 | 0.2 | ... | 0.2 |
| WIDTH (RATIO) | 1.1 | 0.8 | 1.2 | ... | 1.0 |
| HEIGHT (RATIO) | 0.9 | 1.2 | 1.4 | ... | 1.0 |
| IDENTIFICATION SCORE | 0.8 | 0.9 | 0.6 | ... | 0.1 |
| DEGREE OF SIMILARITY | 0.9 | 0.8 | 0.7 | | 0.0 |

MEDICAL IMAGE PROCESSING APPARATUS AND MEDICAL IMAGE PROCESSING METHOD

CLAIM OF PRIORITY

The present application claims priority from Japanese Patent Application JP 2020-013424 filed on Jan. 30, 2020, the content of which are hereby incorporated by references into this application.

BACKGROUND OF THE INVENTION

The present invention relates to a medical image processing apparatus and a medical image processing method for detecting a lesion candidate from a medical image acquired by a medical image imaging apparatus and, more particular, to technology to re-extract a lesion candidate based on a region modified by an operator.

With medical image imaging apparatus typified by ultrasonic diagnostic equipment, larger amounts of medical images are acquired. This increases the burdens on medical professionals such as laboratory technicians and radiologists involved in taking and diagnostically interpreting the medical images. For the purpose of reducing the burdens on the medical professionals, So-called CAD (Computer Aided Detection/Diagnosis) is being more and more developed, in which a computer is used to detect and show lesion candidates from medical images in order to provide support for diagnostic imaging.

Japanese Unexamined Patent Application Publication NO. 2015-154918 discloses determining whether or not a false positive is given based on an anatomical position of a lesion candidate detected in an ultrasonic image, in order to reduce error detection by CAD.

However, Japanese Unexamined Patent Application Publication NO. 2015-154918 gives no consideration to a modification by an operator to a region including a lesion candidate detected by CAD, and for addition of a new region. If there is deficiency or excess in the region detected by CAD, this results in the need for re-imaging and re-interpreting an image of the detected region, and thus another burden is put on the operator who is a medical professional.

SUMMARY OF THE INVENTION

It is accordingly an object of the present invention to provide a medical image processing apparatus and a medical image processing method enabling a reduction in burden of re-imaging and re-interpretation of a medical image.

To achieve this object, the present invention provides a medical image processing apparatus for processing a medical image, including: a detection section that detects, from the medical image, a candidate region which is a region including a lesion candidate or target tissue, and that calculates an identification score for the candidate region; a designated region acquisition section that acquires a designated region which is a region designated by an operator; and a redetection section that calculates an identification score for the designated region based on the designated region and multiple predefined regions which are regions used in a process of detecting the candidate region.

The present invention also provides a medical image processing method that is performed by a medical image processing apparatus for processing a medical image. The method includes: a detection step of detecting, from the medical image, a candidate region which is a region including a lesion candidate or target tissue, and calculating an identification score for the candidate region; a designated region acquisition step of acquiring a designated region which is a region designated by an operator; and a redetection step of calculating an identification score for the designated region based on the designated region and multiple predefined regions which are regions used in a process of detecting the candidate region.

According to the present invention, a medical image processing apparatus and a medical image processing method are provided which enable a reduction in burden of re-imaging and re-interpretation of a medical image.

DETAILED DESCRIPTION OF THE PREFERRED EMBODIMENTS

Preferred embodiments and examples of a medical image processing apparatus and a medical image processing method according to the present invention will now be described with reference to the accompanying drawings. It is noted that, throughout the following description and the accompanying drawings, like reference sings indicate elements having like functions, and a repetitive description is omitted.

First Embodiment

Figure 1:
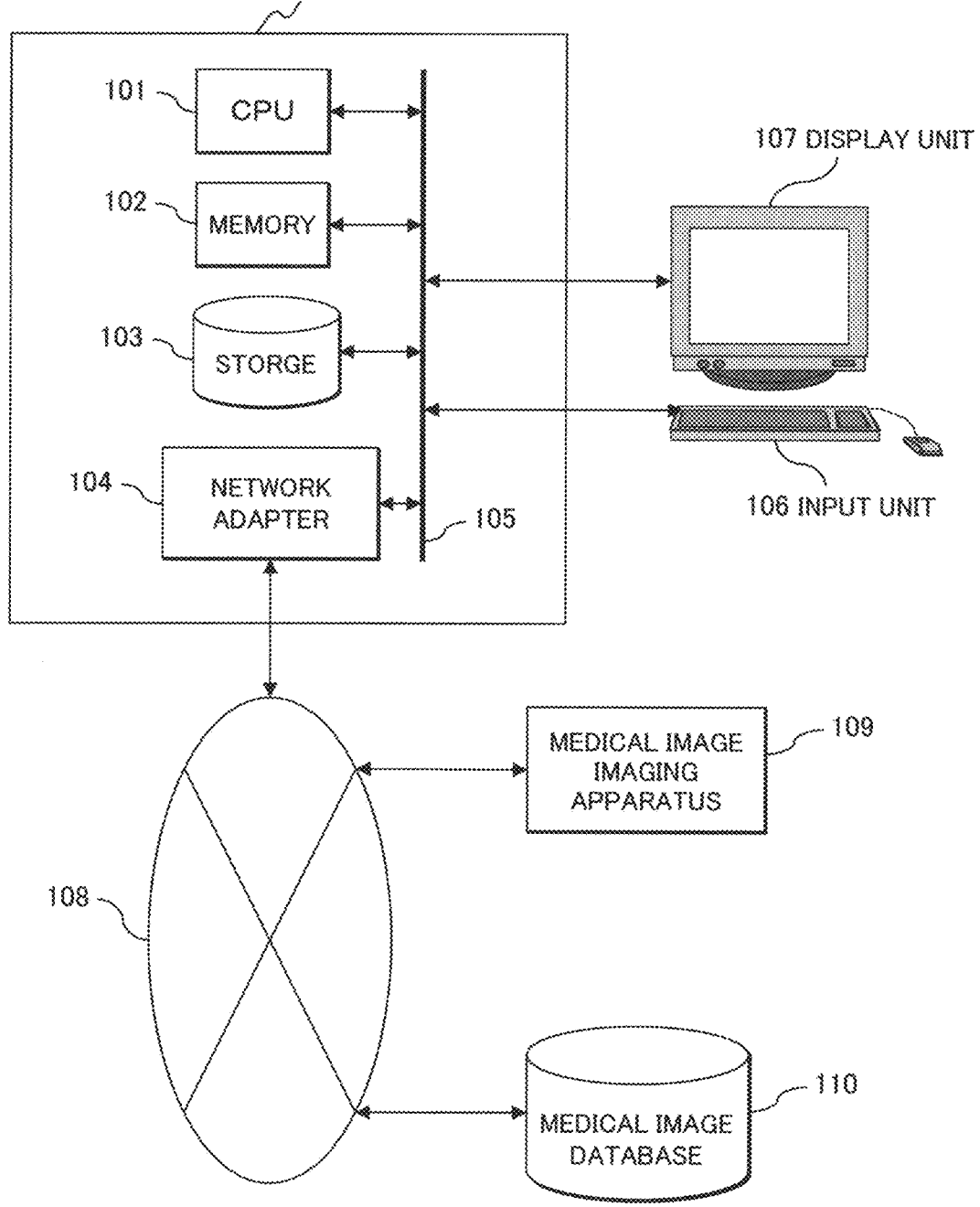
FIG. 1 is a diagram illustrating an example hardware configuration of a medical image processing apparatus according to a first embodiment.

An example hardware configuration of a medical image processing apparatus 100 according to the embodiment is described with reference to FIG. 1. The medical image processing apparatus 100 is a so-called computer, which specifically, is configured to include a CPU (Central Processing Unit) 101, memory 102, storage 103 and a network adapter 104, all of which are connected via a bus 105 in a such a manner as to be able to receive and transmit signals. The medical image processing apparatus 100 is also connected to an input unit 106 and a display unit 107 in such a manner as to be able to receive and transmit signals. Further, the medical image processing apparatus 100 is connected to a medical image imaging apparatus 109 and a medical image database 110 via the network adapter 104 and a network 108 in such a manner as to be able to receive and transmit signals. The expression "to be able to receive and transmit signals" as used herein may refer to a state in which signals can be electrically or optically passed mutually or from one to another without regard to a wireless or wired connection.

The CPU 101 is an apparatus that reads a system program and the like stored in the storage 103 to control the operation of each element. The CPU 101 loads and executes a program stored in the storage 103 and data required for program execution, into the memory 102. The storage 103 is an apparatus that stores a program executed by the CPU 101 and data required for program execution, and, more specifically, an apparatus that performs writing to/reading from a recording apparatus such as HDD (Hard Disk Drive), SSD (Solid State Drive), and the like or a recording medium such as IC card, SD card, DVD, and the like. Various items of data including data required for program execution is also transmitted and received through the network 108 such as LAN (Local Area Network). The memory 102 stores a program executed by the CPU 101, progress of computation processing, and the like.

The display unit 107 is an apparatus on which a result of program execution and the like are displayed, which specifically is a liquid crystal display or the like. The input unit 106 is an operation device used by an operator to provide operational instructions to the medical image processing apparatus 100, which specifically is a keyboard, a mouse, and the like. The mouse may be any other pointing device such as a trackpad, a trackball, and the like. If the display unit 107 is a touch panel, the touch panel functions as the input unit 106. The network adapter 104 is provided for connection of the medical image processing apparatus 100 to the network 108 such as LAN, telephone lines, the internet, and the like.

The medical image imaging apparatus 109 is an apparatus that acquires a medical image, such as a tomographic image and the like, into which a form of a lesion site or the like is imaged. Specifically, the medical image imaging apparatus 109 is ultrasound diagnostic equipment, radiographic X-ray equipment, X-ray CT (Computed Tomography) equipment, MRI (Magnetic Resonance Imaging) equipment, PET (Positron Emission Tomography) equipment, and the like. Stacking a plurality of tomographic images may create a three-dimensional medical image. The medical image database 110 is a database system to store medical images acquired by the medical image imaging apparatus 109.

Figure 2:
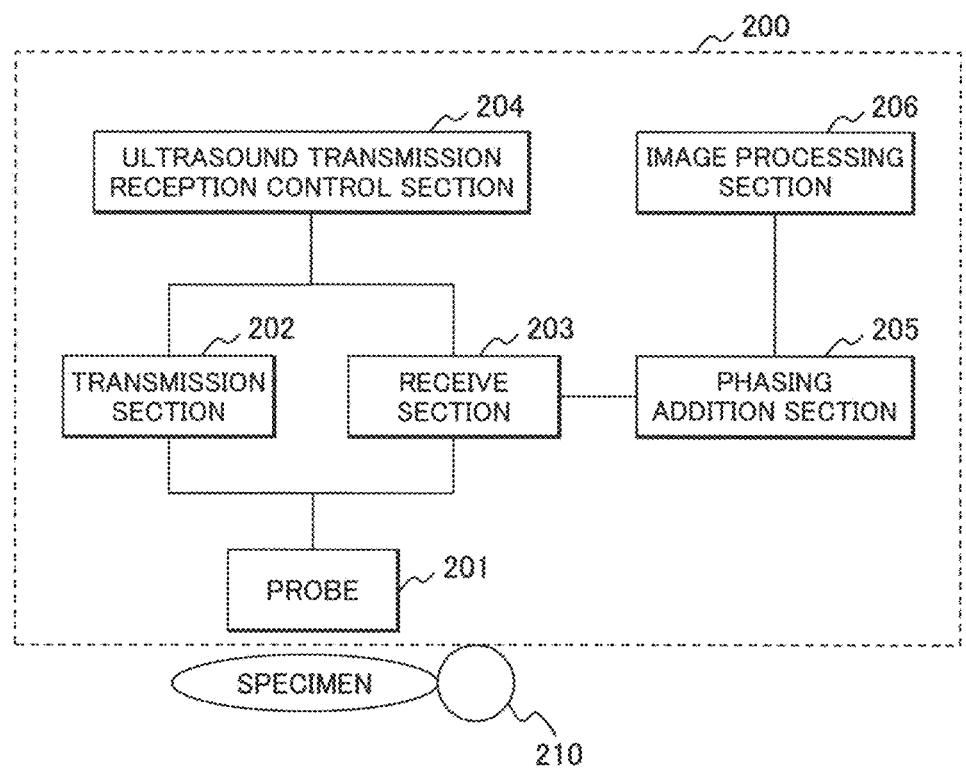
FIG. 2 is a diagram illustrating an example configuration of ultrasonic diagnostic equipment as an example of a medical image imaging apparatus.

Ultrasound diagnostic equipment 200 which is an example of the medical image imaging apparatus 109 is described with reference to FIG. 2. The ultrasound diagnostic equipment 200 include a probe 201, a transmission section 202, a receive section 203, an ultrasound transmission reception control section 204, a phasing addition section 205, and an image processing section 206.

The probe 201 applies an ultrasound wave to a specimen 210 based on a signal transmitted from the transmission section 202, detects the ultrasound wave reflected in the specimen 210, i.e., a so-called reflected echo, and then transmits to the receive section 203 a signal in response to the reflected echo. The transmission section 202 and the receive section 203 are controlled by the ultrasound transmission reception control section 204, and transmit and receive signals from and to the probe 201. The phasing addition section 205 performs phasing and addition on the signal in response to the reflected echo transmitted to the receive section 203, and the analog-to-digital conversion to generate RF (Radio Frequency) signal frame data on a time series basis. Then, the phasing addition section 205 transmits the RF signal frame data to the image processing section 206. The image processing section 206 maps the RF signal frame data generated on a time series basis onto a two-dimensional space in order to generate an ultrasound tomographic image. The generated ultrasound tomographic image is used as a medical image for diagnosis.

Figure 3:
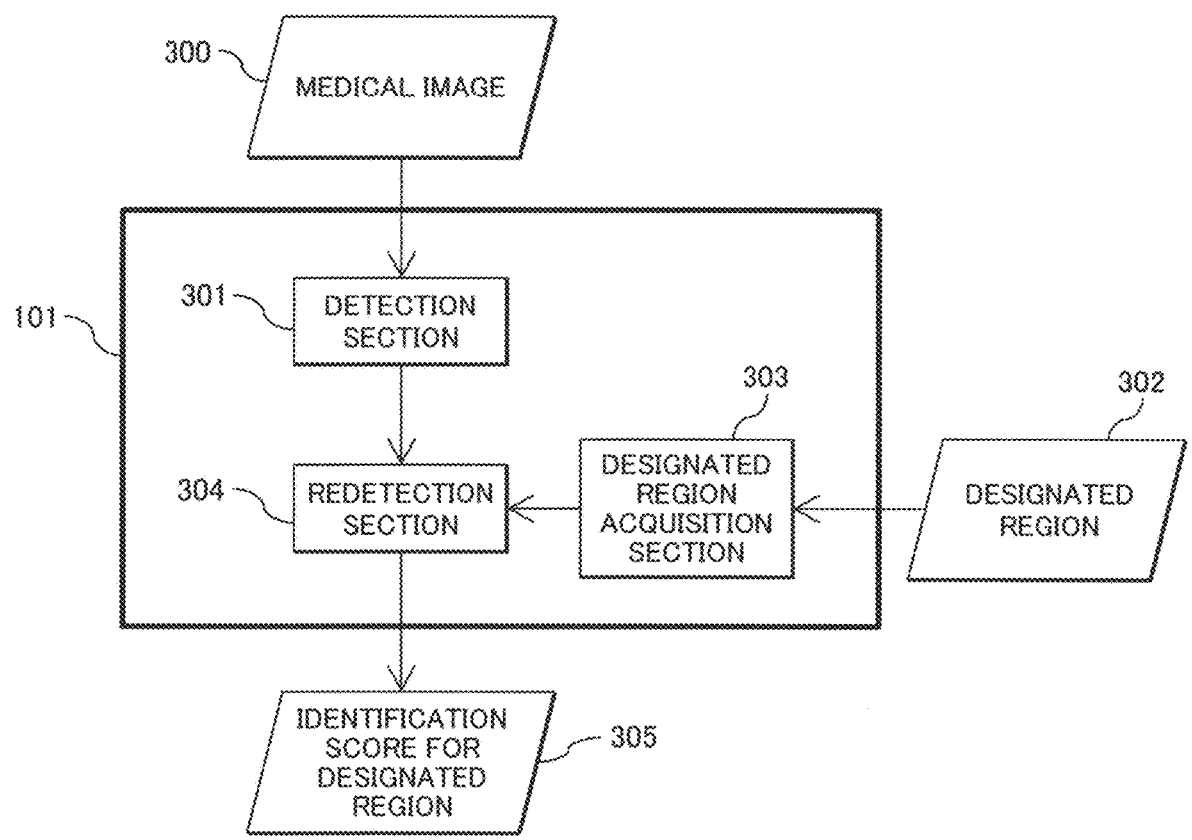
FIG. 3 is a functional block diagram according to the first embodiment.

Referring to FIG. 3 for a functional block diagram describing an essential part of the embodiment. It is noted that the functions may be configured with dedicated hardware using ASIC (Application Specific Integrated Circuit), FPGA (Field-Programmable Gate Array) and/or the like, or with software running on the CPU 101. The case where each function is configured with software is described hereafter. In the embodiment, a detection section 301, a designated region acquisition section 303 and a redetection section 304 are included. The following is a description on each section.

The detection section 301 detects, from a medical image 300, a candidate region which is a region including a lesion candidate or target tissue. And, the detection section 301 calculates an identification score for the candidate region. In short, the detection section 301 functions as so-called CAD. The medical image 300 is acquired by the medical image imaging apparatus 109 or by being read from the medical image database 110. The lesion candidate or target tissue included in the candidate region may be designated through the input unit 106 by an operator. The identification score is an index including at least one of the degree of abnormality, the degree of malignancy, the likelihood of tissue classification, the likelihood of lesion category, and the like. The degree of abnormality denotes a probability of a lesion or a degree of deviation from normal tissue, in which the index takes a value of one if a lesion is present, and takes a value of zero if the tissue is normal. The degree of malignancy denotes a degree of lesion progression, in which the index takes a value of one if the lesion is malignant, and takes a value of zero if the lesion is benign or the tissue is normal. The likelihood of tissue classification denotes a probability that target tissue is predetermined tissue. For example, in a breast test, the likelihood of tissue classification denotes a probability that target tissue is an anatomical tissue such as of mammary gland, fat, major pectoral muscle, costal bone, and the like. The likelihood of lesion category denotes a probability that a lesion candidate falls under a predetermined lesion category, i.e., denoting a probability that a lesion candidate falls under a lesion category defined in accordance with any guideline and/or the like, a disease name of lesion, and/or the like.

Figure 4:
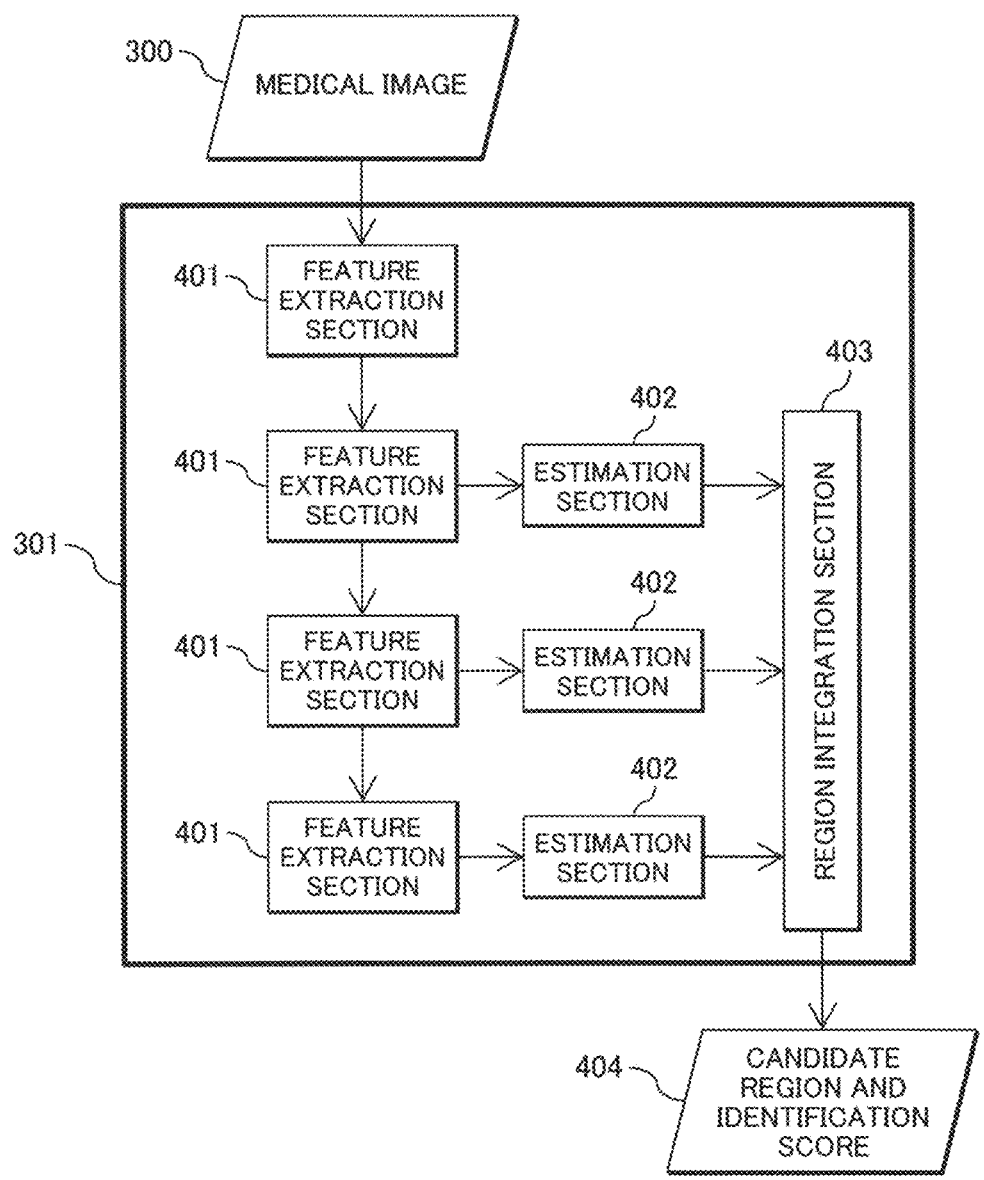
FIG. 4 is a diagram illustrating an example configuration of a detection section.

An example configuration of the detection section 301 is described with reference to FIG. 4. The detection section 301 may be configured to use an object detection neural network capable of simultaneously estimating a candidate region and an identification score, such as, e.g., SSD (Single Shot multi-box Detector), YOLO (You Only Look Once), and the like. The detection section 301 illustrated in FIG. 4 includes feature extraction sections 401, estimation sections 402 and a region integration section 403. It is noted that the detection section 301 pre-learns numerous medical images including known lesions and tissue.

The feature extraction sections 401 perform convolution processing, activation processing, pooling processing, normalization processing, and/or the like in order to calculate multiple feature amount maps from the medical image 300, and then transmit them to the estimation sections 402.

The estimation sections 402 perform convolution processing on the feature amount maps transmitted from the feature extraction sections 401, in order to estimate candidate regions each including a lesion candidate or target tissue, and identification scores for the candidate regions.

Figure 5:
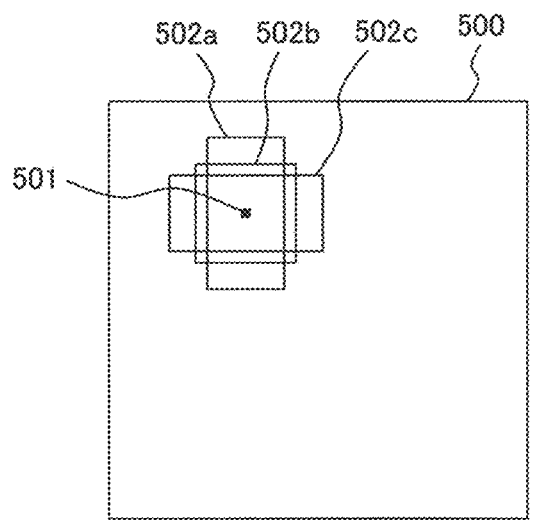
FIG. 5 is a diagram for a supplementary explanation on the processing at an estimation section.

A supplementary explanation is given on the processing at each estimation section 402 with reference to FIG. 5. The estimation section 402 sets multiple predefined regions 502a to 502c for a pixel of interest 501 in the feature amount map 500 calculated at the feature extraction section 401. The predefined regions 502a to 502c may differ from each other in a center position and a size including an aspect ratio. Further, the number and shape of predefined regions 502 are not limited to three and a rectangular shape illustrated in FIG. 5. It is noted that the predefined regions 502 are set similarly for each of the multiple pixels of interest 501.

Further, the estimation section 402 performs the convolution processing on the feature amount map 500 in order to estimate an identification score for each of the multiple predefined regions 502. The result estimated is output in a form such as, e.g., of an estimation result 503, and then transmitted to the region integration section 403. The estimation result 503 is a result in which an identification score is estimated for each of the n predefined regions 502. The estimation result 503 also includes the amounts of vertical and horizontal translations of the center position of each predefined region 502 from the pixel of interest 501, and height and width dimensions of the predefined region 502. For example, a first region in the estimation result 503 has: a center position parallel moved by horizontally 0.2 and vertically 0.4 from the pixel of interest 501; and a width of 0.2 and a height of 0.8, and an identification score is estimated at 0.8.

The region integration section 403 outputs the candidate region and identification score 404 based on the estimation results 503 transmitted from the estimation sections 402. Specifically, first, the predefined region 502 in which the identification score included in the estimation result 503 is equal to or greater than a predetermined threshold value is extracted. Subsequently, NMS (Non-Maximum Suppression) and/or the like is used to inhabit a plurality of predefined regions 502 from being extracted for the same lesion candidate. Specifically, the degree of similarity representing an extent of overlap between a predefined region with a maximum identification score and other predefined regions is calculated. And, of the other predefined regions, a predefined region(s) with the degree of similarity at or above the predetermined threshold value is deleted. For the degree of similarity, for example, IoU (Intersection-over-Union) is used. And, the predefined region(s) which is not deleted based on the degree of similarity is output as a candidate region together with the identification score.

Referring again to FIG. 3, the designated region acquisition section 303 acquires a designated region 302 which is a region designated by the operator. The operator uses the input unit 106 to designate the designated region 302 on the medical image 300.

The redetection section 304 calculates a designated region identification score 305 based on the multiple predefined regions 502 and the designated region 302.

Figure 6:
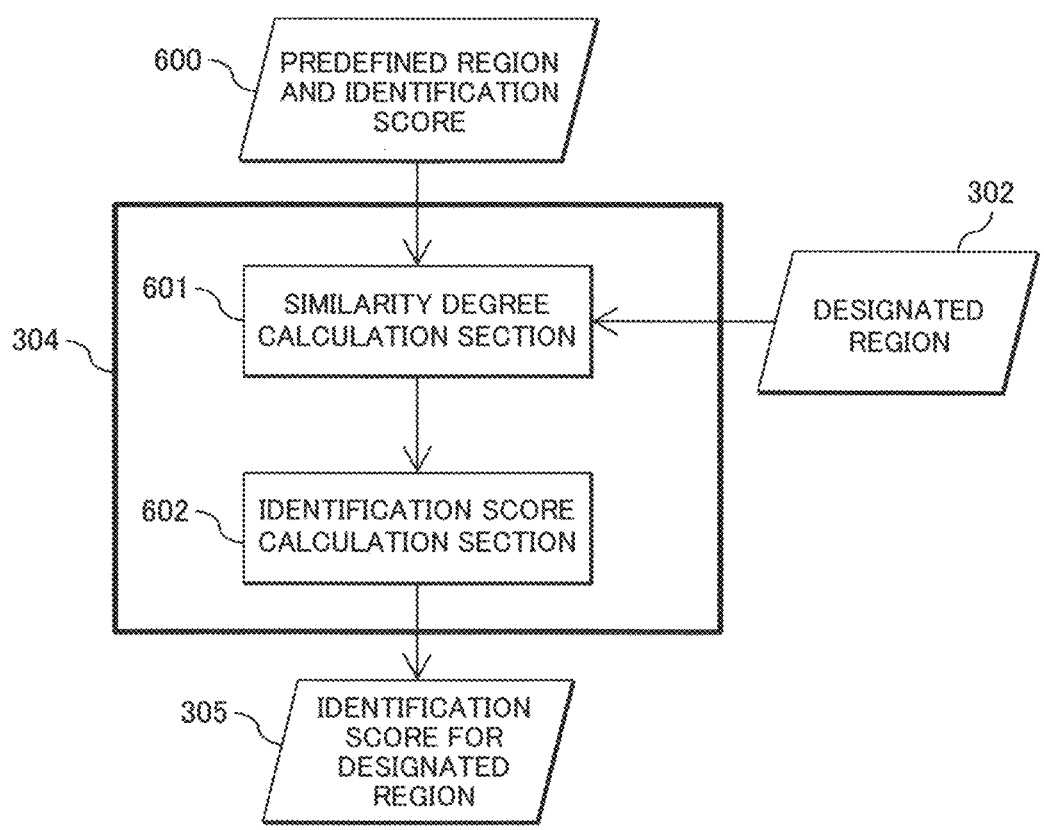
FIG. 6 is a diagram illustrating an example configuration of a redetection section.

An example configuration of the redetection section 304 is described with reference to FIG. 6. The redetection section 304 illustrated in FIG. 6 has a similarity degree calculation section 601 and an identification score calculation section 602. The similarity degree calculation section 601 calculates a degree of similarity between the designated region 302 and each of the multiple predefined regions 502. For the degree of similarity, at least one of, for example, IoU, DICE coefficient, Jaccard coefficient, Simpson coefficient, a center distance of regions, the area of region, an aspect ratio, and the like is used.

The identification score calculation section 602 calculates an identification score for the designated region 302 based on an identification score for each of the multiple predefined regions 502 and each degree of similarity. An identification score Iowa for the designated region 302 is calculated by using, for example, the following equation.

$$\text{Score} = \Sigma(W_i \cdot s_i) / \Sigma(W_i) \quad (1)$$

where $s_i$ is an identification score for each of the multiple predefined regions 502, and $w_i$ is each degree of similarity between the designated region 302 and each of the multiple predefined regions 502.

Figure 7:
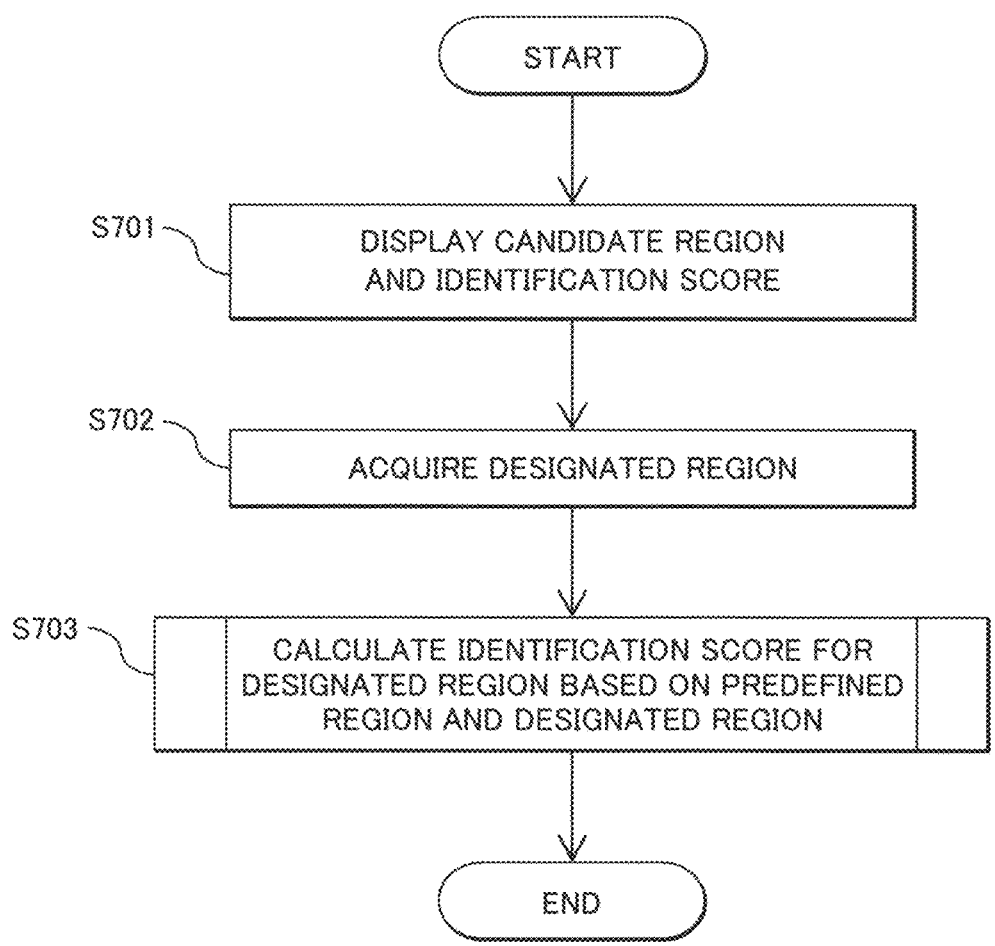
FIG. 7 is a flow diagram showing an example of the processing according to the first embodiment.

An example of the processing according to the embodiment is described with reference to FIG. 7.

(S701)

The detection section 301 detects a candidate region from the medical image 300, and calculates and displays an identification score for the candidate region on the display unit 107.

Figure 8:
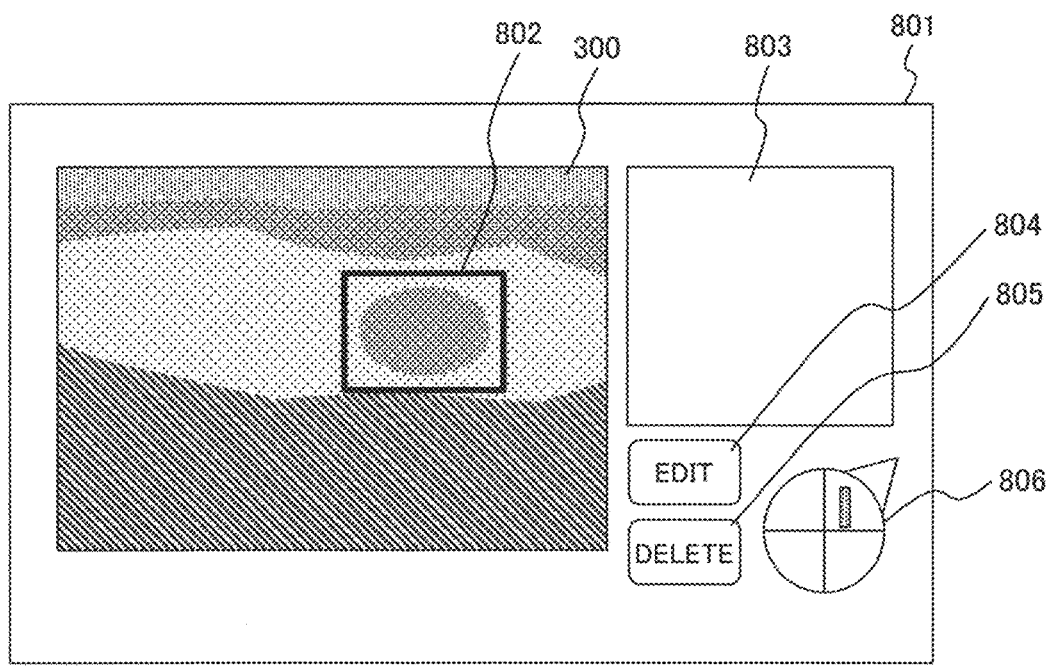
FIG. 8 is a diagram illustrating an example of the display screens according to the first embodiment.

An example of the display screens according to the embodiment is described with reference to FIG. 8. The medical image 300 and the candidate region 802 including the lesion candidate are displayed on the display screen 801 in FIG. 8. The identification score for the candidate region 802 is also displayed in an identification result 803, and an edit button 804 and a deletion button 805 are displayed. Further, a test point icon 806 may be displayed.

The edit button 804 is used to make a switch to the mode for editing the candidate region 802 in order to generate a designated region. A deletion button 805 is used to delete the candidate region 802. A test point icon 806 is an icon representing a test point of the medical image 300 displayed on the display screen 801. FIG. 8 illustrates an icon simulating a left breast, in which a vertically rectangular shape on the icon represents a position of the probe, i.e., a test point. In FIG. 8, an upper left portion of the left breast is illustrated as a test point.

(S702)

The designated region acquisition section 303 acquires a designated region designated by the operator.

Editing of the designated region is described with reference to FIG. 9. In response to selection of the edit button 804 on the display screen 801 in FIG. 8, the edit button 804 changes in color, and multiple control points 901 are displayed on the frame of the candidate region 802. The changing in color of the edit button 804 indicates that a switching to the mode to edit the candidate region 802 has occurred. The multiple control points 901 are points moved through operation of a mouse pointer 902, and they are used to edit the candidate region 802 to generate a designated region. After the control points 901 are moved, when the edit button 804 is re-selected, the edit button 804 restores to the original color and the designated region is decided. Thus, the designated region acquisition section 303 acquires a position and a size of the designated region.

Figure 9:
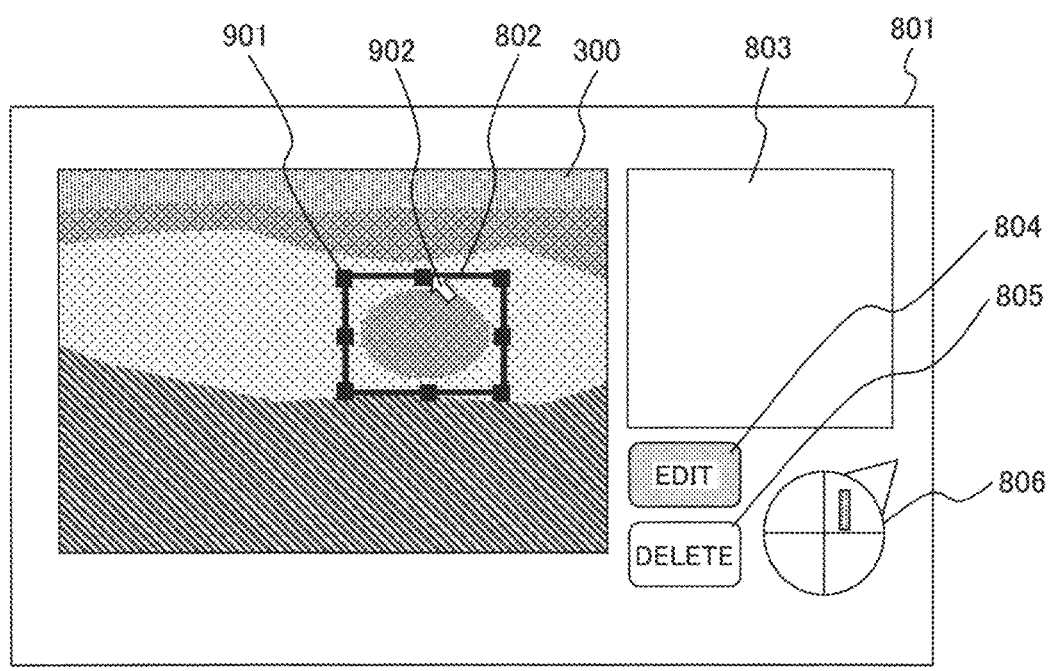
FIG. 9 is a diagram illustrating editing of a designated region.
Figure 10:
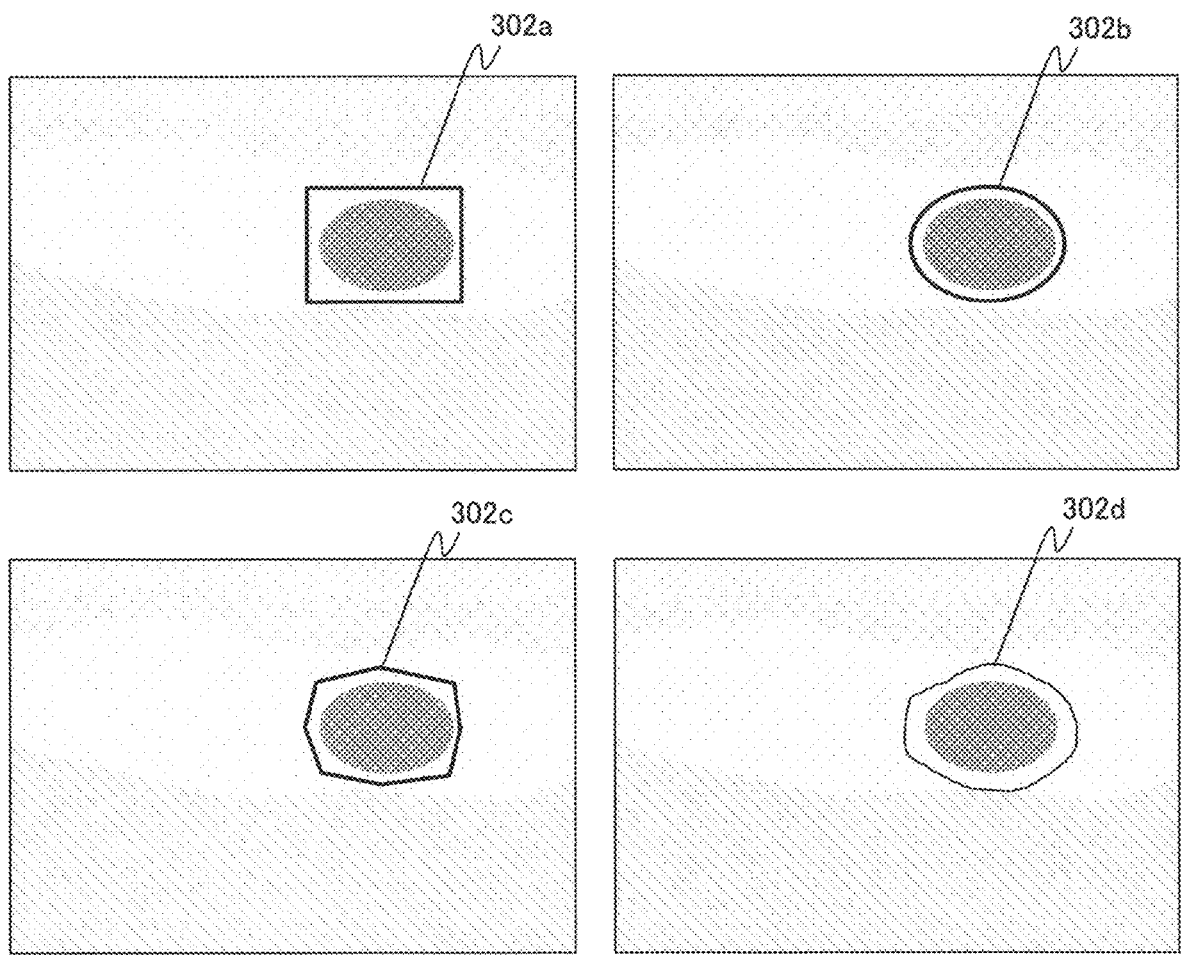
FIG. 10 illustrates examples of shapes of a designated region.

It is noted that the shape of the designated region is not limited to a rectangular shape illustrated in FIG. 9. Examples of the shape of the designated region 302 are explained with reference to FIG. 10. As regards the shape of the designated region 302, a designated region 302b of an elliptic or circular shape, a designated region 302c of a polygonal shape, a designated region 302d of a closed region by a free form curve, and the like, may be used other than the designated region 302a of a rectangular shape. The operator may change the shape of the designated region 302 with reference to a shape of the lesion candidate visually identified on the medical image 300 by the operator oneself.
(S703)

The redetection section 304 calculates an identification score for a designated region based on the multiple predefined regions used in the process of detecting the candidate region 802 by the detection section 301, and the designated region acquired in S702.

Figure 11:
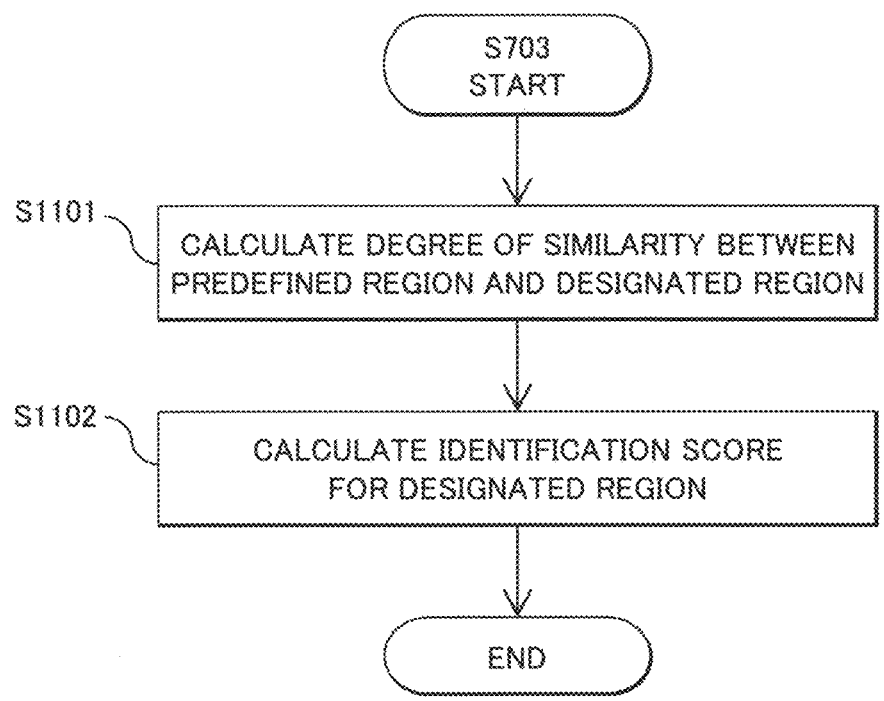
FIG. 11 is a flow diagram of an example of the processing of calculating an identification score for a designated region.

An example of the processing flow in the step is described with reference to FIG. 11.
(S1101)

The similarity degree calculation section 601 calculates the degree of similarity between a designated region and each of multiple predefined regions. For example, IoU is used for the degree of similarity. The degree of similarity takes a value of one if both the regions match each other, and takes a value of zero if there is not overlap.
(S1102)

The identification score calculation section 602 calculates an identification score for the designated region 302 based on an identification score for each of the multiple predefined regions 502 and each degree of similarity. For the calculation of the identification score for the designated region 302, at least one of an average or weighted average, logistic regression, SVM, neural network, and the like may be used, and, for example, Equation (1) may be used. It is noted that, for use of Equation (1), the predefined region 502 for use in the identification score calculation may be limited to having a higher degree of similarity to the designated region 302. For example, the predefined region 502 may be limited to having a higher degree of similarity than a predetermined threshold value or to having any degree of similarity falling within predetermined ranks. Limiting the number of predefined regions 502 enables a reduction in computational complexity.

Figure 12:
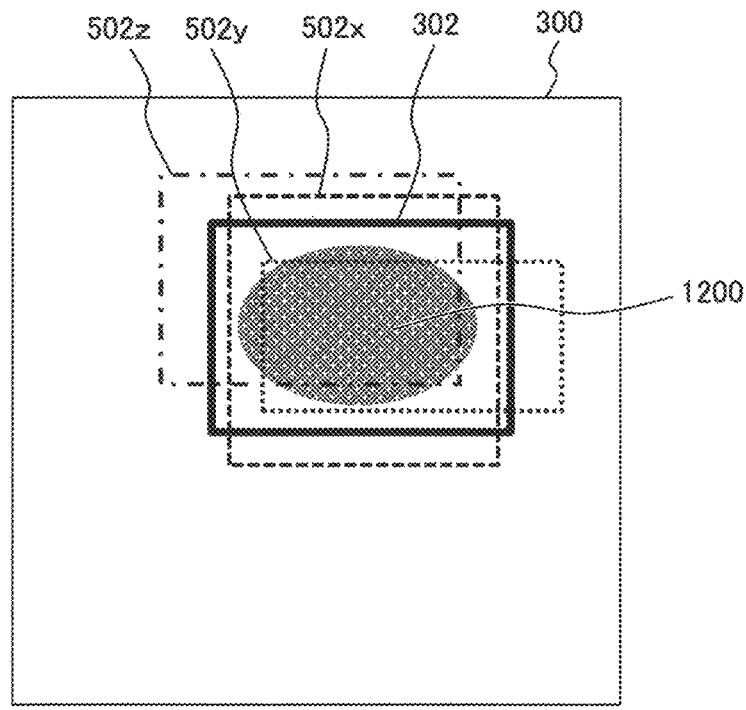
FIG. 12 is a diagram for a supplementary explanation on the processing at an identification score calculation section.

A supplementary explanation is given on the processing at the identification score calculation section 602 with reference to FIG. 12. FIG. 12 illustrates: a lesion candidate 1200 visually identified on the medical image 300 by the operator; the designated region 302 designated by the operator; and predefined regions 502x to 502z each of which has the degree of similarity to the designated region 302 at or above a predetermined threshold value of 0.7. FIG. 12 also illustrates an estimation result 1201 into which the estimation result 503 illustrated in FIG. 5 is sorted according to the degrees of similarity. For calculation of the identification score for the designated region 302, when predefined regions are limited to the predefined regions 502x to 502z with the degree of similarity at or above a predetermined threshold value of 0.7, Equation (1) is rewritten as follows.

$$\text{Score} = (w_x \cdot s_x + w_y \cdot s_y + w_z \cdot s_z)/(w_x + w_y + w_z) \quad (2)$$

where $s_x$, $s_y$, $s_z$ are the identification scores for the respective predefined regions 502x to 502z, and $w_x$, $w_y$, $w_z$ are the degrees of similarity between the respective predefined regions 502x to 502z and the designated region 302.

The calculation result of the identification score for the designated region 302 is displayed on the display unit 107. For example, the identification score for the designated region 302 may be displayed in the identification result 803 of the display screen 801 illustrated in FIG. 9. It is noted that if the identification score is the degree of malignancy or the likelihood of lesion category, a result of sorting into either malignancy or benign or into which lesion category through threshold processing may be displayed.

Because of the processing flow described above, even if there is deficiency or excess in a region detected by the detection section functioning as CAD, the identification score for the designated region designated by the operator is calculated. Consequently, the numbers of re-imaging and re-interpretation of the medical image can be reduced, and thus a reduction in burden on the operator who is a medical professional is enabled.

Although the embodiments according to the present invention has been described, the present invention is not limited to the embodiments and encompasses various modifications. For example, the above embodiments have been described in detail in order to provide a clear understanding of the present invention, and the present invention is not necessarily limited to including all the components and configurations described above.

REFERENCE SIGNS LIST

100: medical image processing apparatus, 101: CPU, 102: memory, 103: storage, 104: network adapter, 105: bus, 106: input unit, 107: display unit, 108: network, 109: medical image imaging apparatus, 110: medical image database, 200: ultrasound diagnostic equipment, 201: probe, 202: transmission section, 203: receive section, 204: ultrasound transmission reception control section, 205: phasing addition section, 206: image processing section, 210: specimen, 300: medical image, 301: detection section, 302, 302a to 302d: designated region, 303: designated region acquisition section, 304: redetection section, 305: designated region identification score, 401: feature extraction section, 402: estimation section, 403: region integration section, 404: candidate region and identification score, 500: feature amount map, 501: pixel of interest, 502, 502a to 502c, 502x to 502z: predefined region, 503: estimation result, 600: predefined region and identification score, 601: similarity degree calculation section, 602: identification score calculation section, 801: display screen, 802: candidate region, 803: identification result, 804: edit button, 805: deletion button, 806: test point icon, 901: control point, 902: mouse pointer, 1200: lesion candidate, 1201: estimation result into which estimation result is sorted

What is claimed is:

1. A medical image processing apparatus for processing a medical image, comprising:
a processor that, when executing at least one program, configures the processor to:
detect, from the medical image, a candidate region which is a region including a lesion candidate or target tissue, and calculate an identification score for the candidate region;
acquire a designated region which is a region designated by an operator;
calculate an identification score for the designated region based on the designated region and multiple predefined regions which are regions used in a process of detecting the candidate region;
calculate a degree of similarity between the designated region and each of the multiple predefined regions, and calculate an identification score for the designated region based on the degree of similarity and an identification score for each of the multiple predefined regions; and
calculate the identification score for the designated region as $\Sigma(W_i \cdot s_i)/\Sigma(W_i)$ where $s_i$ is an identification score estimated by convolution processing for each of the multiple predefined regions, and $W_i$ is the degree of similarity.

2. The medical image processing apparatus according to claim 1, wherein the processor is further configured to use only the identification score $s_i$ for a predefined region with the degree of similarity $W_i$ at or above a predetermined threshold value.

3. The medical image processing apparatus according to claim 1, wherein the designated region is generated by deforming the candidate region.

4. The medical image processing apparatus according to claim 1, wherein the designated region has any one of a plurality of shapes including a rectangular shape, an elliptic shape, a circular shape, a polygonal shape, and a closed region by a free form curve.

5. The medical image processing apparatus according to claim 1, wherein the identification score is an index including at least one of a degree of abnormality, a degree of malignancy, a likelihood of tissue classification, and a likelihood of lesion category.

6. A medical image processing method that is performed by a medical image processing apparatus for processing a medical image, comprising the steps of:

detecting, from the medical image, a candidate region which is a region including a lesion candidate or target tissue, and calculating an identification score for the candidate region;

acquiring a designated region which is a region designated by an operator;

calculating an identification score for the designated region based on the designated region and multiple predefined regions which are regions used in a process of detecting the candidate region;

calculating a degree of similarity between the designated region and each of the multiple predefined regions, and calculating an identification score for the designated region based on the degree of similarity and an identification score for each of the multiple predefined regions; and calculating the identification score for the designated region as $\Sigma(W_i \cdot s_i)/\Sigma(W_i)$ where $s_i$ is an identification score estimated by convolution processing for each of the multiple predefined regions, and $W_i$ is the degree of similarity.

* * * * *